United States Patent
Dembkowski et al.

(10) Patent No.: US 8,450,488 B2
(45) Date of Patent: May 28, 2013

(54) PROCESS FOR THE PREPARATION OF [1-HYDROXY-2-(3-PYRIDINYL)ETHYLIDENE] BISPHOSPHONIC ACID AND HEMIPENTAHYDRATE MONOSODIUM SALT THEREOF

(75) Inventors: Leszek Dembkowski, Pruszcz Gdański (PL); Robert Rynkiewicz, Starogard Gdański (PL); Janusz Rachoń, Gdańsk (PL); Slawomir Makowiec, Gdańsk (PL); Witold Przychodzeń, Gdańsk (PL); Dariusz Witt, Gdańsk (PL)

(73) Assignee: Zaklady Farmaceutyczne Polpharma S.A., Gdansk (PL)

( * ) Notice: Subject to any disclaimer, the term of this patent is extended or adjusted under 35 U.S.C. 154(b) by 1102 days.

(21) Appl. No.: 11/721,334

(22) PCT Filed: Dec. 28, 2005

(86) PCT No.: PCT/PL2005/000085
§ 371 (c)(1),
(2), (4) Date: Jun. 9, 2007

(87) PCT Pub. No.: WO2006/071128
PCT Pub. Date: Jul. 6, 2006

(65) Prior Publication Data
US 2009/0281320 A1    Nov. 12, 2009

(30) Foreign Application Priority Data
Dec. 28, 2004  (PL) .................................. P.371 958

(51) Int. Cl.
*C07F 9/58* (2006.01)
*C07F 9/00* (2006.01)
(52) U.S. Cl.
USPC .......................................... 546/22

(58) Field of Classification Search
USPC ............................................... 546/22
See application file for complete search history.

(56) References Cited

U.S. PATENT DOCUMENTS

| | | | | |
|---|---|---|---|---|
| 2,684,286 | A * | 7/1954 | Krieger | 423/316 |
| 4,407,761 | A * | 10/1983 | Blum et al. | 562/13 |
| 6,410,520 | B2 * | 6/2002 | Cazer et al. | 514/89 |
| 2001/0041690 | A1 * | 11/2001 | Cazer et al. | 514/79 |
| 2003/0195170 | A1 * | 10/2003 | Aronhime et al. | 514/89 |

FOREIGN PATENT DOCUMENTS

| | | |
|---|---|---|
| EP | 1 234 592 A | 9/2002 |
| WO | WO 2005063779 A2 * | 7/2005 |

OTHER PUBLICATIONS

Gossman W L, et al., Three hydrates of the biphosphonate risedronate, consisting of one molecular and two ionic structures, Acta Crystallographica Section C, Jan. 11, 2003, p. m33-m36, vol. C59, International Union of Crystallography, Chester, England.

* cited by examiner

*Primary Examiner* — Janet Andres
*Assistant Examiner* — Timothy R Rozof
(74) *Attorney, Agent, or Firm* — McNeely, Hare & War LLP; William D. Hare

(57) ABSTRACT

The invention relates to a novel process for the preparation of [1-hydroxy-2-(3-pyridinyl)ethylidene]bisphosphonic acid and hemipentahydrate monosodium salt thereof comprising (a) reacting an aqueous solution of 3-pyridyl acetic acid hydrochloride with phosphorus trichloride; (b) removing unreacted phosphorus trichloride; (c) adding water and hydrolyzing; (d) isolating crystalline [1-hydroxy-2-(3-pyridinyl)ethylidene]bisphosphonic acid; (e) suspending said crystalline [1-hydroxy-2-(3-pyridinyl)ethylidene]bisphosphonic acid in water; (f) adding sodium hydroxide, filtering off, and washing; and (g) drying obtained hemipentahydrate monosodium salt of 1-hydroxy-2-(3-pyridinyl)ethylidene] bisphosphonic acid.

26 Claims, 1 Drawing Sheet

PROCESS FOR THE PREPARATION OF [1-HYDROXY-2-(3-PYRIDINYL)ETHYLIDENE] BISPHOSPHONIC ACID AND HEMIPENTAHYDRATE MONOSODIUM SALT THEREOF

CROSS-REFERENCE TO RELATED APPLICATIONS

This is a National Stage Application of International Patent Application No. PCT/PL 2005/000085, with an international filing date of Dec. 28, 2005, which is based on Polish Patent Application No. P.371 958, filed Dec. 28, 2004. The contents of both of these specifications are incorporated herein by reference.

BACKGROUND OF THE INVENTION

1. Field of the Invention

The present invention relates to a process for the preparation of [1-hydroxy-2-(3-pyridinyl)ethylidene]bisphosphonic acid and of the hemipentahydrate monosodium salt thereof useful in the treatment of osteoporosis.

2. Description of the Related Art

[1-hydroxy-2-(3-pyridinyl)ethylidene]bisphosphonic acid (1), also shown in FIG. 1,

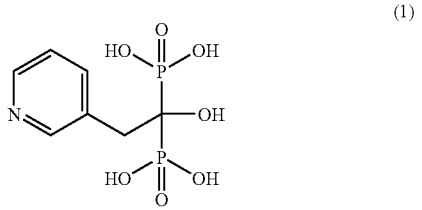 [SMILES: O=P(O)(O)C(O)(Cc1cccnc1)P(=O)(O)O]

(1)

is otherwise known under the international non-proprietary name (INN) as risedronic acid.

The hemipentahydrate monosodium salt of [1-hydroxy-2-(3-pyridinyl)ethylidene]bisphosphonic acid is otherwise known under the international non-proprietary name (INN) as risedronate sodium.

Risedronate sodium is one of many bisphosphonates, which form a large group of medicines useful in the treatment of disorders caused by abnormal calcium metabolism, i.e., osteoporosis or Paget disease. Specifically, risedronate sodium is used in the treatment of postmenopausal osteoporosis, and is particularly used to reduce the risk of vertebral body fracture and femoral neck fracture.

The process for the preparation of [1-hydroxy-2-(3-pyridinyl)ethylidene]bisphosphonic acid is based mainly on the reaction of 3-pyridyl acetic acid with phosphorous acid and phosphorus chloride. Chemical literature references and patent descriptions specify that chlorobenzene, fluorobenzene and methanesulphonic acid are used as solvents in these routes of synthesis; the yield referred to in the literature is not greater than 52%.

Specifically, the European patent EP 0 186 405 B1 claims a reaction of 3-pyridyl acetic acid with phosphorous acid in chlorobenzene, where phosphorus trichloride is added.

Moreover, the Polish patent application P.346517 discloses a method for the preparation of risedronic acid by reacting 3-pyridyl acetic acid hydrochloride with phosphorous acid and phosphorus trichloride in chlorobenzene or fluorobenzene. The solvent is then removed, risedronic acid isolated, and reacted with an alkali metal or ammonium hydroxide, bicarbonate or carbonate, to yield an alkali metal salt or the ammonium salt of risedronic acid. The procedure, carried out in accordance with the description of Polish patent application P.346517, allows for obtaining risedronic acid with a yield of 49-50%.

Both 3-pyridyl acetic acid and phosphorous acid are not soluble in chlorobenzene and fluorobenzene. The entire process takes place in a heterogeneous system, which makes intermixing of reactants difficult. Isolating of the product is done by decantation of chlorobenzene or fluorobenzene from an amorphous oily reaction product. The yield in these experiments is not repeatable and ranges between 10 and 47%. The use of methanesulphonic acid as the solvent gives a product with a low yield (see, *J. Org. Chem.* 1995, 60; 8310-8312). An additional problem when carrying out the procedures is that methanesulphonic acid is highly reactive and toxic.

BRIEF SUMMARY OF THE INVENTION

The use of phosphorus trichloride as solvent and reagent in the process for the preparation of [1-hydroxy-2-(3-pyridinyl) ethylidene]bisphosphonic acid and hemipentahydrate monosodium salt thereof surprisingly allows the reaction to be carried out in a homogeneous system. Additionally, the yield of the reaction is 82% for the risedronic acid and 67% for the monosodium salt thereof if proper pH and drying conditions are ensured. Crystallization of risedronic acid facilitates the removal of the phosphoric acid, phosphorous acid, and hydrochloric acid produced in the reaction.

Consistently, the present invention provides a novel process for the preparation of [1-hydroxy-2-(3-pyridinyl)ethylidene]bisphosphonic acid and hemipentahydrate monosodium salt thereof.

BRIEF DESCRIPTION OF THE DRAWINGS

The objects and advantages of the present invention will become more readily apparent after reading the ensuing description of the non-limiting illustrative embodiment and viewing the accompanying drawings, in which.

DETAILED DESCRIPTION OF THE INVENTION

Figure 1:
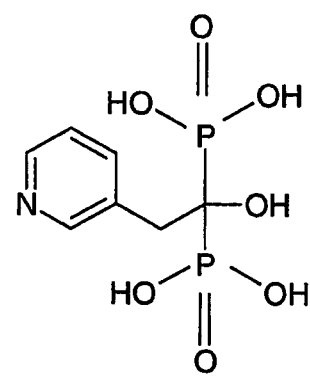
FIG. 1 shows a chemical structure of [1-hydroxy-2-(3-pyridinyl)ethylidene]bisphosphonic acid.
Figure 2:
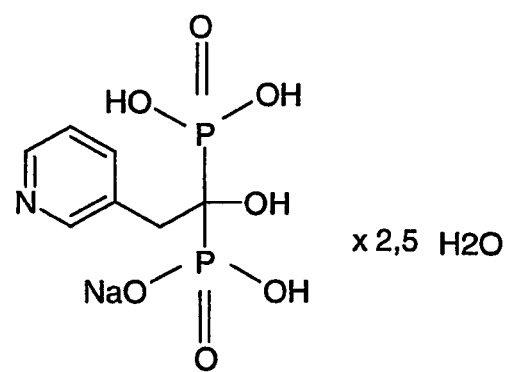
FIG. 2 shows a chemical structure of hemipentahydrate monosodium salt of [1-hydroxy-2-(3-pyridinyl)ethylidene]bisphosphonic acid.

The present invention provides a process for the preparation of [1-hydroxy-2-(3-pyridinyl)ethylidene]bisphosphonic acid wherein aqueous solution of 3-pyridyl acetic acid hydrochloride is added dropwise to phosphorus trichloride at a temperature of 0-5° C. in the initial stage of the process. The mixture is then reacted and excess phosphorus trichloride is removed. Water is then added and the mixture is hydrolyzed. The then isolated, crystalline [1-hydroxy-2-(3-pyridinyl)ethylidene]bisphosphonic acid is suspended in water, and 45% aqueous sodium hydroxide is added. The resulting monosodium salt precipitate is filtered off and dried. The molar ratio of 3-pyridyl acetic acid hydrochloride, phosphorus trichloride and water used in the reaction is 1:6:7.4 (moles).

In order to obtain a product in the form of hemipentahydrate monosodium salt, the reaction requires pH of 4.9-5.0. Drying of the salt is performed at a temperature of 25-30° C.

Drying in an appropriate temperature ensures that the finished product has the form of hemipentahydrate monosodium salt of [1-hydroxy-2-(3-pyridinyl)ethylidene]bisphosphonic acid (2).

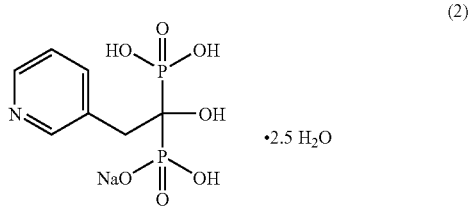

(2)

The following examples are provided to illustrate the invention. The examples are not meant limit the scope of the invention as defined in the claims.

Example 1

Process for the preparation of [1-hydroxy-2-(3-pyridinyl)ethylidene]bisphosphonic acid Aqueous solution of 35.75 g (0.206 moles) of 3-pyridyl acetic acid hydrochloride was added dropwise with vigorous mixing over 1 hour at a temperature of 0-5° C. into 169.93 g (1.23 moles) of phosphorus trichloride cooled to a temperature of 0-5° C. The reaction mixture was then slowly heated to a temperature of 75-80° C. and maintained at this temperature until the reaction mixture in its solid state is obtained. Excess phosphorus trichloride used in the reaction was distilled off under reduced pressure. Then, 200 mL of water were added and the mixture was hydrolyzed by boiling for 6 hours. After cooling, the mixture was filtered, washed with water, and dried. As a result, 48 g (82% yield) of [1-hydroxy-2-(3-pyridinyl)ethylidene]bisphosphonic acid was obtained.

$^1$H NMR ($D_2O$) δ=3.35 (t., J (H, P)=11.9 Hz, 2H, $CH_2$); 7.42 (dd., J=8.1 Hz, J=4.9 Hz, 1H, CH); 8.00 (d., J=8.1 Hz, 1H, CH); 8.42 (dd., J=4.9 Hz, J=1.5 Hz, 1H, CH); 8.59 (d., J=1.5 1H, CH). $^{13}$C NMR ($D_2O$) δ=40.8 ($CH_2$); 78.2 (t., J=128 Hz, C); 127.8 (CH); 138.8 (t., J=8 Hz, C); 144.6 (CH); 150.5 (CH); 155.1 (CH). $^{31}$P NMR ($D_2O$) δ=18.2

Example 2

Process for the preparation of hemipentahydrate monosodium salt of [1-hydroxy-2-(3-pyridinyl)ethylidene]bisphosphonic acid 20 g of [1-hydroxy-2-(3-pyridinyl)ethylidene]bisphosphonic acid was suspended in 100 mL of water and heated to a temperature of 100-102° C., and 6.58 g of 45% aqueous sodium hydroxide was then added dropwise until pH 4.9-5.0 was obtained. This reaction mixture was boiled for 2 hours, and 1.25 g of activated carbon was added. Next, the reaction mixture was filtered, and the filtrate was cooled to a temperature of 25° C. and maintained at this temperature for 4 hours. The resulting precipitate was filtered, washed with water and methanol and dried at a temperature of 25-30° C. As a result, 16.5 g (67% yield) of hemipentahydrate monosodium salt of [1-hydroxy-2-(3-pyridinyl)ethylidene]bisphosphonic acid were obtained.

$^1$H NMR ($D_2O$) δ=3.35 (t., J (H, p)=12.2 Hz, 2H, CH2); 7.54 (bm., 1H, CH); 8.16 (bm., 1H, CH); 8.41 (d., J=4.9 Hz, 1H, CH); 8.60 (s., 1H, CH). $^{13}$C NMR ($D_2O$) δ=40.8 ($CH_2$); 78.1 (t, J=130 Hz, C); 128.7 (CH); 140.2 (L, J=8 Hz, C); 147.7 (CH); 148.0 (CH); 152.3 (CH). $^{31}$P NMR ($D_2O$) δ=17.8.

What is claimed is:

1. A process for the preparation of [1-hydroxy-2-(3-pyridinyl)ethylidene]bisphosphonic acid and hemi-pentahydrate monosodium salt thereof, the process comprising reacting aqueous solution of 3-pyridinyl acetic acid hydrochloride with phosphorus trichloride that is added dropwise at a temperature of 0-5° C., removing excess phosphorus trichloride, adding water to hydrolyze products of the reaction, isolating crystalline [1-hydroxy-2-(3-pyridinyl)ethylidene]bisphosphonic acid and suspending in water, adding soda lye, obtaining a precipitate, and filtering off, washing, and drying the precipitate to yield hemi-pentahydrate monosodium salt of [1-hydroxy-2-(3-pyridinyl)ethylidene]bisphosphonic acid.

2. The process according to claim 1, wherein the molar ratio of 3-pyridinyl acetic acid hydrochloride, phosphorus trichloride, and water is 1:6:7.4 (moles).

3. The process according to claim 1, wherein the reaction, in which the salt is produced, is carried out at pH 4.9-5.0.

4. The process according to claim 1, wherein drying of the salt is carried out at a temperature of 25-30° C.

5. A process for the preparation of [1-hydroxy-2-(3-pyridinyl)ethylidene]bisphosphonic acid, the process consisting of:
   (a) reacting an aqueous solution of 3-pyridinyl acetic acid hydrochloride with excess phosphorus trichloride used both as reagent and solvent, whereby critically forming a homogenous mixture;
   (b) removing unreacted phosphorus trichloride;
   (c) adding water, and hydrolyzing; and
   (d) isolating crystalline [1-hydroxy-2-(3-pyridinyl)ethylidene]bisphosphonic acid.

6. The process of claim 5, wherein in step (a) an aqueous solution of 3-pyridinyl acetic acid hydrochloride is added dropwise to phosphorus trichloride at a temperature of 0-5° C.

7. The process of claim 5, wherein in step (a) the addition of an aqueous solution of 3-pyridinyl acetic acid hydrochloride is conducted over a period of at least 1 hour and after the 3-pyridinyl acetic acid hydrochloride is added, the reaction mixture is heated to a temperature of 75-80° C. and maintained at this temperature until no liquid is visible.

8. The process of claim 5, wherein in step (b) the unreacted phosphorus trichloride is distilled off under reduced pressure.

9. The process of claim 5, wherein in step (c) water is added and the mixture is hydrolyzed by boiling.

10. The process of claim 5, wherein in step (d) the crystalline [1-hydroxy-2-(3-pyridinyl)ethylidene]bisphosphonic acid is isolated by filtering off, washing with water, and drying.

11. The process of claim 5, wherein in step (a) the molar ratio of 3-pyridinyl acetic acid hydrochloride to phosphorus trichloride to water is 1:6:7.4.

12. The process of claim 5, wherein in step (d) the crystalline [1-hydroxy-2-(3-pyridinyl)ethylidene]bisphosphonic acid is obtained in at least an 80% yield.

13. A process for the preparation of hemipentahydrate monosodium salt of [1-hydroxy-2-(3-pyridinyl)ethylidene]bisphosphonic acid, the process consisting of:
   (a) reacting an aqueous solution of 3-pyridinyl acetic acid hydrochloride with excess phosphorus trichloride used both as reagent and solvent, whereby critically forming a homogenous reaction mixture;
   (b) removing unreacted phosphorus trichloride;
   (c) adding water and hydrolyzing;
   (d) isolating crystalline [1-hydroxy-2-(3-pyridinyl)ethylidene]bisphosphonic acid;

(e) suspending said crystalline [1-hydroxy-2-(3-pyridinyl)ethylidene]bisphosphonic acid in water;

(f) adding sodium hydroxide, filtering off, and washing; and (g) drying obtained hemipentahydrate monosodium salt of [1-hydroxy-2-(3-pyridinyl)ethylidene]bisphosphonic acid at a temperature of between 25 and 30° C.

14. The process of claim 13, wherein in step (a) an aqueous solution of 3-pyridinyl acetic acid hydrochloride is added dropwise to phosphorus trichloride at a temperature of 0-5° C.

15. The process of claim 13, wherein in step (a) the addition of an aqueous solution of 3-pyridinyl acetic acid hydrochloride is conducted over a period of at least 1 hour and after the 3-pyridinyl acetic acid hydrochloride is added the reaction mixture heated to a temperature of 75-80° C. and maintained at this temperature until no liquid is visible.

16. The process of claim 13, wherein in step (b) the unreacted phosphorus trichloride is distilled off under reduced pressure.

17. The process of claim 13, wherein in step (c) water is added and the mixture is hydrolyzed by boiling.

18. The process of claim 13, wherein in step (d) crystalline [1-hydroxy-2-(3-pyridinyl)ethylidene]bisphosphonic acid is isolated by filtering off, washing with water, and drying.

19. The process of claim 13, wherein in step (a) the molar ratio of 3-pyridinyl acetic acid hydrochloride to phosphorus trichloride to water is 1:6:7.4.

20. The process of claim 13, wherein in step (f) sodium hydroxide is added until the pH reaches a value of 4.9-5.0.

21. The process of claim 13, wherein in step (g) the product is optionally washed with water and methanol.

22. The process of claim 13, wherein in step (d) the crystalline [1-hydroxy-2-(3-pyridinyl)ethylidene]bisphosphonic acid is obtained in at least an 80% yield.

23. The process of claim 13, wherein in step (g) the hemipentahydrate monosodium salt of [1-hydroxy-2-(3-pyridinyl)ethylidene]bisphosphonic acid is obtained in at least a 65% yield.

24. A process for the preparation of [1-hydroxy-2-(3-pyridinyl)ethylidene]bisphosphonic acid, the process consisting of:

(a) adding critically dropwise an aqueous solution of 3-pyridinyl acetic acid hydrochloride to excess phosphorus trichloride at a temperature of between 0 and 5° C. to form a homogeneous liquid reaction mixture, wherein the molar ratio of 3-pyridinyl acetic acid hydrochloride to phosphorus trichloride to water is 1:6:7.4, and said phosphorus trichloride is used as both reagent and solvent; heating the homogeneous mixture to a temperature of critically between 75 and 80° C., and maintaining the reaction mixture at that temperature until it solidifies;

(b) removing unreacted phosphorus trichloride;

(c) adding water, and hydrolyzing; and (d) isolating crystalline [1-hydroxy-2-(3-pyridinyl)ethylidene]bisphosphonic acid.

25. A process for the preparation of hemihydrate monosodium salt of [1-hydroxy-2-(3-pyridinyl)ethylidene]bisphosphonic acid, the process consisting of:

(a) adding critically dropwise an aqueous solution of 3-pyridinyl acetic acid hydrochloride to excess phosphorus trichloride at a temperature of between 0 and 5° C. to form a homogeneous liquid reaction mixture, wherein the molar ratio of 3-pyridinyl acetic acid hydrochloride to phosphorus trichloride to water is 1:6:7.4, and said phosphorus trichloride is used as both reagent and solvent; heating the homogeneous mixture to a temperature of critically between 75 and 80° C., and maintaining the reaction mixture at that temperature until it solidifies;

(b) removing unreacted phosphorus trichloride;

(c) adding water and hydrolyzing;

(d) isolating crystalline [1-hydroxy-2-(3-pyridinyl)ethylidene]bisphosphonic acid;

(e) suspending said crystalline [1-hydroxy-2-(3-pyridinyl)ethylidene]bisphosphonic acid in water;

(f) adding sodium hydroxide, filtering off, and washing; and (g) drying obtained hemipentahydrate monosodium salt of [1-hydroxy-2-(3-pyridinyl)ethylidene]bisphosphonic acid at a temperature of between 25 and 30° C.

26. The process of claim 25, wherein the hemi-pentahydrate monosodium salt of [1-hydroxy-2-(3-pyridinyl)ethylidene]bisphosphonic acid obtained in g) is free of monohydrate monosodium salt of [1-hydroxy-2-(3-pyridinyl)ethylidene]bisphosphonic acid.

\* \* \* \* \*